US006565878B2

(12) United States Patent
Schoenfeldt et al.

(10) Patent No.: US 6,565,878 B2
(45) Date of Patent: *May 20, 2003

(54) METHOD FOR PREPARING A NON-FIBROUS POROUS MATERIAL

(75) Inventors: Lars Schoenfeldt, Snekkersten (DK); Brian Nielsen, Hillroed (DK); Josef Ayzma, Koebenhavn (DK)

(73) Assignee: Coloplast A/S, Humlebaek (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/446,902

(22) PCT Filed: Jul. 2, 1998

(86) PCT No.: PCT/DK98/00298

§ 371 (c)(1),
(2), (4) Date: Mar. 17, 2000

(87) PCT Pub. No.: WO99/01166

PCT Pub. Date: Jan. 14, 1999

(65) Prior Publication Data

US 2002/0172708 A1 Nov. 21, 2002

(30) Foreign Application Priority Data

Jul. 2, 1997 (DK) ................................................ 0789/97

(51) Int. Cl.$^7$ .................................................. A61F 13/00
(52) U.S. Cl. ........................ 424/443; 424/424; 424/449
(58) Field of Search ................................. 424/443, 449

(56) References Cited

FOREIGN PATENT DOCUMENTS

| DE | 26 27 708 | | 12/1977 | |
|----|-----------|---|---------|---|
| EP | 0 268 498 | * | 5/1988 | ............. C08F/8/14 |
| EP | 0 269 393 | * | 6/1988 | ............. C08F/8/14 |
| GB | 2 296 250 | | 6/1996 | |
| JP | 01-011141 | | 1/1989 | |
| WO | WO94/04724 | | 3/1994 | |
| WO | WO 95/05204 | * | 2/1995 | ........... A61L/15/16 |
| WO | WO 96/20015 | * | 7/1996 | |

* cited by examiner

Primary Examiner—Thurman K. Page
Assistant Examiner—Isis Ghali
(74) Attorney, Agent, or Firm—Jacobson Holman PLLC

(57) ABSTRACT

A method for preparing a non-fibrous porous material essentially consisting of one or more hydrophilic polymeric components(s) or one or more hydrophilic polymeric component(s) and one or more pharmaceutical medicaments, the method comprising forming an aqueous solution, sol or gel comprising one or more hydrophilic polymers and/or pharmaceutical medicaments, freezing or foaming the solution, dehydrating the frozen or foamed solution leaving a non-fibrous porous material in a solid, porous form, and optionally subjecting the resulting porous material to a dry heat treatment.

16 Claims, No Drawings

METHOD FOR PREPARING A NON-FIBROUS POROUS MATERIAL

BACKGROUND OF THE INVENTION

1. Field of the Invention

The present invention relates to a method for preparing a non-fibrous porous material being swellable but not soluble in water essentially consisting of one or more hydrophilic polymers and/or pharmaceutical water-soluble medicaments, an absorbing article containing such material and the use of such material for the preparation of an absorbing article.

2. Description of the Related Art

Non-fibrous porous materials essentially consisting of one or more hydrophilic polymers and/or pharmaceutical water-soluble medicaments and methods for preparing such materials are disclosed in WO 95/05204 and in JP 01-011141.

One method for preparing such products using a hydrous solution of a hydrophilic polymer such as casein, gelatine, collagen, albumin, fibroin, cellulose, starch, agar, sodium carboxyl methyl cellulose, methyl cellulose, polyvinyl alcohol, polyacrylic acid, or polyacrylamide is disclosed in JP 01-011141. According to JP 01-011141, a surfactant of non-ionic, cationic, anionic or amphoteric type is added to the hydrous solution and then freeze-drying is carried out. The polymer is dispersed in water at a concentration of 0.05 to 50%, and the surfactant is used in amounts of from 0.5–100%.

Another method or preparing such products using a hydrous solution of a hydrophilic polymer such as a synthetic hydrophilic polymer, a polysaccharide or a biological hydrophilic polymer is disclosed in WO 95/05204. According to WO 95/05204, one or more pharmaceutical medicaments and/or hydrophilic polymers are dissolved in water to provide a solution or a sol, a freeze plate is pre-nucleated by passive condensation or by evaporating or atomising water or the aqueous solution of the pharmaceutical medicaments and/or hydrophilic polymers and/or salts, the solution of one or more pharmaceutical medicaments and/or hydrophilic polymers is provided on the pre-nucleated freeze plate, the temperature of which is kept below the freezing point of the atomised water or solution, the solution is frozen to provide an ice sheet comprising the pre-nucleated frozen material, the sheet is freeze dried, and the resulting sheet is optionally cut into pieces of suitable sizes.

WO 96/20015 discloses chitosan salts and a process for the preparation thereof. The chitosan salt may be recovered in a desired form depending on the use for which it is intended, and for use in absorbent personal care products such as a wound dressing it is generally in the form of a discrete particle, fibre or flake. There is no indication of production of a cohesive gel and the content of cross-linker is below 10 weight percent.

GB 2 296 250 discloses a method for-preparing water-swellable, water-insoluble chitin/chitosan salts having improved absorption properties by forming a mixture of a chitosan, water, an acid, and, optionally, a crosslinking agent, recovering the formed chitosan salt from the mixture and, optionally, treating said recovered chitosan salt with heat under humid conditions. Freeze drying of these hydrogels results in stiff and brittle xerogels which are unpleasant in contact with human skin or wounds.

A water absorbing porous material can be prepared from cross-linked CMC powders by the freeze drying technique disclosed in WO 95/05204. However, xerogels produced in this manner have no cohesion after rehydration due to the formation of a sol gel.

These properties render such materials less suitable for use if they are not fully enclosed as they tend to disintegrate when absorbing water. Such disintegration render such materials less suitable for use in wound dressings as it is highly desirable that the absorbing material has a sufficient cohesion to be removed as an integrate piece without leaving residues on the skin or in the wound.

WO 94/04724 discloses a method of producing a fibre or film by extruding an aqueous solution of a water-soluble polymer into a gaseous medium to form fibre or film. The extruded fibre or film is dried and cross-linked at a temperature in the range of 125 to 250° C. to a degree sufficient that the crosslinked fibre or film is water-insoluble. The resulting fibres or film are intended for use in preparing webs for use in absorbing articles.

EP 0 269 393 discloses preparation of fibre or film by dry extrusion of a solution of a linear polymer formed from a water soluble blend of mono ethylenically unsaturated monomers comprising plasticizing monomer.

EP 0 268 498 discloses a water absorbent water insoluble polymeric element such as a fibre, film, coating, bonding layer or foam made by forming a substantially linear polymer by polymerization of water soluble ethylenically unsaturated monomer blends and then crosslinking the same.

DE 26 27 708 discloses water swellable fibres made from water-insoluble acrylic acid polymerization.

The above references are silent with respect to preparation of an absorbing material having a very high absorbing capacity and having, at the same time, a very high degree of cohesion rendering the material suitable for use in an article being in direct contact with the skin or the surface of a wound Thus, there is still a need for an absorbing material having a very high absorbing capacity and having, at the same time, having a very high degree of cohesion rendering the same suitable for use in an article being in direct contact with the skin or the surface of a wound. Examples of absorbing articles are, e.g., disposable diapers, incontinence articles, sanitary napkins or the like having an absorbing core or an absorbing wound dressing.

It has surprisingly been found that the novel porous materials prepared according to the present invention are swellable but not soluble in water and are very suitable for use as absorbing components in, e.g., wound dressings.

BRIEF SUMMARY OF THE INVENTION

The present invention relates to a method for preparing a non-fibrous porous material being swellable but not soluble in water essentially consisting of one or more hydrophilic polymers and/or pharmaceutical water-soluble medicaments; a non-fibrous material which may be produced by the method; a dressing comprising a non-fibrous porous material essentially consisting of one or more hydrophilic polymers and/or pharmaceutical medicaments; and the use of such a material for the preparation of a dressing or an absorbent article.

DETAILED DESCRIPTION OF THE INVENTION

In a first aspect, the invention relates to a method for preparing a non-fibrous porous material being swellable but not soluble in water, the material essentially consisting of one or more natural or semi-synthetic hydrophilic polymers or one or more hydrophilic polymeric component(s) and one or more pharmaceutical medicaments, the method comprising forming an aqueous solution or sol gel comprising one or more hydrophilic polymers or one or more hydrophilic polymeric component(s) and one or more pharmaceutical medicaments, forming an object of the solution or sol gel having a desired shape and dehydrating the same leaving a non-fibrous porous material in a solid, porous form, and subjecting the resulting porous material to a dry heat treatment.

A material produced in this manner shows superior absorbing capacity and does not disintegrate upon absorbing water. It is believed that the dry heat treatment causes formation of cross-links in the non-fibrous porous material being responsible for the superior properties with respect to absorbing capacity combined with a cohesion ensuring non-disintegration upon swelling.

In a preferred embodiment of the method of the invention, one or more hydrophilic polymeric component(s) or one or more hydrophilic polymeric materials component(s) and one or more pharmaceutical medicaments are dissolved or solubilized in water to provide a sol gel, the gel sol is placed on a surface, the temperature of which is to be kept below the freezing point of water or the gel sol, freezing the solution or sol gel to provide an ice structure comprising the frozen material and removing the water selectively leaving the solid materials of the solution or sol gel in the form of a porous structure and subjecting the resulting porous material to a dry heat treatment.

It is especially preferred that the freeze plate is pre-nucleated and that the sol gel is placed on the pre-nucleated freeze plate which enables a fine control of the structure of the frozen ice structure.

In accordance with the invention, the water may preferably be removed by freeze-drying or by solvent extraction.

When carrying out the heat treatment in the method of the invention, the process may be allowed to proceed at a relatively longer time at a low temperature or a relatively shorter time at an elevated temperature. It is preferred to keep the material at an elevated temperature of from 40 to 220° C. for a period of from 1 minute to several hours. The temperature is preferably held at from 50 to 70° C. for at least 15 minutes.

The final heat treatment causes a "secondary crosslinking". The secondary crosslinking can occur in the step where the solvent is removed (in the freeze-drying process or if the water removed by evaporation).

Such a material shows a superior absorbing capacity and provides a coherent gel which does not disintegrate upon absorbing water is and may be removed after use as a whole.

In one preferred embodiment of the invention the material comprises two or more hydrophilic polymers and optionally pharmaceutical medicaments comprising polyionic/polyfunctional materials having opposite charges.

This means, that at least two polymers in the material must have opposite charges, but the material could for example comprise one cationic polymer, two anionic polymers and one pharmaceutical medicament. Optionally, the material could comprise polymer components having the same di-, tri or oligomer component of the opposite charge.

It is preferred to use a polyionic/polyfunctional anionic material comprising at least one polyanionic group such as: sulphates, thiosulphates, acids, acid salts or phosphates or functional groups such as acid chlorides or anhydrides, and at least one polycationic group such as a primary, secondary or tertiary amine or phosphine group. One of two polymer components could also be a pharmaceutical medicament having an ionic charge. Another option is that at least one of the materials is amphoteric (such as some polypeptides and amino acids).

The polymers are dissolved forming aqueous solutions. Normally, a cationic polymer needs an acid in order to be dissolved, but if the cationic polymer is present in the form of a salt, it is normally soluble in water. For example, chitosan is only soluble in water when an acid is present (the acid protonates chitosan), whereas chitosan lactate (which is protonated) is directly soluble in water. An anionic polymer is normally present in the form of a salt and is therefore dissolved in water. For example, instead of using the insoluble alginic acid, an alginate is used (alginate is the salt of alginic acid). If the anionic polymer is alginic acid, it is dissolved by converting it into a salt by dissolving it in a basic aqueous solution.

Thus, a polymer may be converted from a non-ionic (and insoluble) state to cationic (and soluble) state by addition of acid. One specific example of such a material is, e.g., chitosan.

Acids used to dissolve a cationic polymer could be any lower carboxylic acid having from 1 to 7 carbon atoms preferably 1 to 4 carbon atoms. The organic acid could be both mono-, di or trivalent acids such as formic acid, acetic acid, glycolic acid, glyoxylic acid, propionic acid, acrylic acid, butyric acid, pyruvic acid, oxalic acid or lactic acid.

If the cationic polymer is dissolved as a salt, where the counter ion is inorganic (for example chitosan chloride), which is water soluble (no addition of acid is necessary to dissolve the cationic polymer), one could add (dissolve) to the cationic polymer solution (or to the anionic polymer solution before mixing or to the mixed dispersion) some organic acid salt such as sodium acetate, which enables a secondary crosslinking. When the cationic polymer is a salt with an inorganic counter ion, there is however also another option. Instead of adding an organic acid salt one could add a low molecular weight amine or ammonia. For example, if chitosan chloride (cationic) is dissolved in water, ammonia could be added to this solution (or to the anionic polymer solution before mixing or to the mixed dispersion).

At last the cationic polymer could be present as a salt, where the counter ion is organic such as chitosan lactate, which is soluble in water and the lactate ion enables the secondary crosslinking. In this situation no addition of any molecule should be necessary. The organic counter ion could be any carboxylic acid salt having from 1 to 7 carbon atoms such as formic acid, acetic acid, glycolic acid, glyoxylic acid, propionic acid, propenoic acid, butyric acid, pyruvic acid, oxalic acid or lactic acid.

Thereafter, the solutions are mixed forming a gel dispersion. When the solutions are mixed, the anionic groups of the anionic polymer combine with the cationic groups of the cationic polymer forming a crosslinking between the two polymers. This reaction is in the present context designated "primary crosslinking". Normally this reaction occurs momentarily when the solution is mixed. By continuing the mixing, the solution is turned into a dispersion or a "sol gel". The mixing time may vary from a few seconds to several minutes for obtaining a "homogeneous" dispersion. The mixing process may be any convenient mixing process known per se capable of forming a dispersion or a sol gel.

When a "homogeneous" dispersion/sol gel is obtained, it is frozen, solvent removed and heat treated as described earlier in the detailed description of the invention. "Secondary crosslinking" during in the heat treatment. Such crosslinking may be effected by establishing ionic links between the polymeric chains or by establishing of covalent bonds, e.g., by formation of ester bonds by cleavage of water from carboxylic and hydroxylic groups forming ester groups.

"Secondary crosslinking" can occur when at least two polyionic/polyfunctional materials having opposite charges are present, at least 15% by weight of the polyionic/polyfunctional materials have the same charge. The term "poly" is used in the present context to designate at least two units.

It is also an aspect of the invention to have two different natural or semi-synthetic hydrophilic polymers or polymeric component(s) having opposite functionality/charge in any desired ratio from 15:85 to 85:15, more preferably form 20:80 to 80:20.

In a further embodiment of the invention, a pharmaceutical medicament may participate in the crosslinking process as one of the parts as long as such crosslinking does not have any adverse effect on the pharmaceutical effect thereof.

In accordance with the invention, the multifunctional/ionic component enabling crosslinking preferably is present in an amount of from 20 to 100% by weight. It is often preferred to combine two hydrophilic polymers in a proportion by weight of from 40:60 to 60:40.

Such a material also shows a superior absorbing capacity and provides a coherent gel which does not disintegrate upon absorbing water and may be removed after use as a whole.

Examples of anionic groups linked to an anionic polymer which may be used for the invention and which may undergo "secondary crosslinking" with a polymer of opposite charge are groups such as sulphates or thiosulphates, acids or acid salts such as alginates or phosphates or functional groups such as acid chlorides or anhydrides.

Cationic groups linked to a cationic polymer may, e.g., be amines, phosphines or imines. The amine groups may be primary, secondary or tertiary alkyl, cycloalkyl or aromatic amines. The term "alkyl" is used in the present context to designate straight or branched alkyl groups having up to 6 carbon atoms, preferably 1–4 carbon atoms, such as methyl, ethyl, propyl, isopropyl, a butyl, a isobutyl, an pentyl or hexyl group. Cycloalkyl may comprise from 5 to 7 carbon atoms. An example of an aromatic amine is phenylamine.

The best results are achieved when using sulphates, acids, acid salts or phosphates as anionic groups and primary amine groups as cationic groups attached directly to a polymer backbone, preferably a polysaccharide.

The materials comprising anionic groups or cationic groups (or both) could be polysaccharides, synthetic or semisynthetic polymers, polypeptides, proteins, salts, cellular and extracelluar materials.

The polysaccharides (and derivatives thereof) used according to the invention may be selected from polysaccharides such as cellulose derivatives such as CMC or derivatives thereof, chitin/chitosan or derivatives thereof, starches or derivatives thereof, alginates, pectin/pectat, gallan, hyaluronic acid or salts thereof, ionic derivatives of glucans, carragenans, glycomannan, xanthan, guar or derivatives thereof or locust bean gum, glucosamines, glucosaminoglycans such as heparan sulphate, chondroitin sulphate or keratan sulphate, and proteins and polypeptides such as heparin or collagen.

The hydrophilic polymer or material used according to this embodiment of the invention preferably comprises at least two of the following polysaccharides chitin/chitosan or their derivatives thereof, calcium/sodium alginate, pectin/pectate, carragenan, CMC, other derivatives of cellulose, hyaloronic acid, derivatives of starches and/or chondroitin sulphate.

The polymers used according to the invention preferably have an overall ionic charge in an aqueous solution.

In another preferred embodiment of the invention, the material can be made of only one hydrophilic polymer (or optionally more). The polymers to be used in this embodiment of the invention is(are) preferably selected from polysaccharides and derivatives thereof such as CMC, hydroxyethylcellulose, chitin/chitosan and alginates.

A preferred hydrophilic component is CMC or a mixture of CMC and an alginate or chitosan or its derivatives.

It is especially preferred that the polysaccharides comprises CMC and alginate in the form of a sodium alginate or a mixture of sodium and calcium alginates.

Furthermore, it is especially preferred according to the invention that the polysaccharide is chitosan.

In accordance with another aspect of the invention the solution to be frozen may essentially be based on pharmaceutical medicaments or a mixture of the hydrophilic polymers mentioned earlier in the description and pharmaceutical medicaments. Suitable pharmaceutical medicaments are, for example, a cytochine such as a growth hormone or a polypeptide growth factor such as TGF, FGF, PDGF, EGF, IGF-1, IGF-2, colony stimulating factor, transforming growth factor, nerve stimulating growth factor and the like.

Further suitable additives present in the solution to be frozen are cell lysates preferably from keranocytes or fibroblasts.

A growth hormone or a polypeptide growth factor shows an enhancing effect on wound healing.

It is also advantageous that a dressing according to the invention comprises wound healing associated indicator(s), cushions or similar device for treatment or prophylaxis of formation of wounds and/or skin anormalities.

This enables for a combined medical treatment of the wound and an easy and sterile application of the active ingredients, e.g., by incorporating active ingredients such as a cytochine such as growth hormone or a polypeptide growth factor giving rise to the incorporation of such active substances in a form being apt to local application in a wound in which the medicament may exercise its effect on the wound, other medicaments such as bacteriostatic or bactericidal compounds, e.g., iodine, iodopovidone complexes, chloramine, chlorohexidine, silver salts such as sulphadiazine, silver nitrate, silver acetate, silver lactate, silver sulphate or silver chloride, zinc or salts thereof, metronidazol, sulpha drugs, and penicillins, tissue-healing enhancing agents, e.g., RGD tripeptides and the like, proteins, amino acids such as taurine, vitamins such ascorbic acid, enzymes for cleansing of wounds, e.g., pepsin, trypsin and the like, proteinase inhibitors or metalloproteinase inhibitors such as Illostat or ethylene diamine tetraacetic acid, cytotoxic agents and proliferation inhibitors for use in, for example, surgical insertion of the product in cancer tissue and/or other therapeutic agents which optionally may be used for topical application, pain relieving agents such as lidocaine or chinchocaine, emollients, retinoids or agents having a cooling effect which is also considered an aspect of the invention.

In a second aspect, the invention relates to a non-fibrous porous material being swellable but not soluble in water.

The material comprises two or more hydrophilic polymers and optionally pharmaceutical medicaments. When the polymers are dissolved, they must have opposite charges in the solutions.

In a third aspect, the invention relates to a non-fibrous porous material whenever prepared by the method of the invention.

In a fourth aspect, the invention relates to a dressing comprising a non-fibrous porous material essentially consisting of one or more hydrophilic polymers or one or more hydrophilic polymers and one or more pharmaceutical medicaments, the material being producible by the method of the invention.

In a fifth aspect, the invention relates to the use of a non-fibrous porous material essentially consisting of one or more hydrophilic polymers or one or more hydrophilic polymers and one or more pharmaceutical medicaments wherein the porous material has been subjected to dry heat treatment for the preparation of a dressing or an absorbent article such as a wound dressings, an article for preventing post surgery adhesion or for haemostasis, disposable diapers, incontinence articles, sanitary napkins and the like having absorbent cores. This material may constitute a part of a product or be the product itself.

The term "sol gel" is used in the present context to designate an aqueous dispersion of hydrated crosslinked particles. The particles act like independent particles—not inter-cross-linked. The crosslinking bonds are either covalent or ionic. The liquid phase comprises pure water or an aqueous solution.

The term "Xerogel" is used in the present context to designate a porous hydrophilic material having any desired shape and any desired internal morphology comprising a dry (dehydrated) porous matrix stretching throughout the material. A xerogel may be a water disintegrating or a water insoluble xerogel. A primary crosslinked xerogel is a disintegrating gel because it is prepared by dehydration of a sol gel and/or a polymer solution. Hence, it consists of independent polymer chains or dry sol gel particles. A secondary crosslinked xerogel is water absorbing but water insoluble because the dry sol gel particles are inter-crosslinked the building blocks of the cell walls are crosslinked to each other. Thus, such a gel forms a cohesive gel when soaked with water.

In the present context growth hormone is intended to designate any growth hormone which is applicable in accordance with the invention such as human, bovine, ovine, porcine, equine, salmon or tuna growth hormone or analogues or derivatives thereof such as shortened or extended growth hormones such as methionyl growth hormone. A growth hormone is preferably human growth hormone.

The invention is explained more in detail with reference to the below working examples disclosing embodiments of the invention which are to be considered illustrative only of principles of the invention. As all suitable modifications and equivalents may be resorted to, the examples are not to be considered as limiting the scope of the invention set forth in the appended claims.

Experimental Part

EXAMPLE 1

Two crosslinked xerogels having controlled morphology and similar chemical composition were produced. One xerogel was produced by the method of present invention and the other was produced by a method including freezing and ion exchange after freeze drying. The production method of the present invention resulted in a xerogel having a higher absorbing capacity.

A: Preparation of Stock Solutions

Three stock solutions were prepared by dissolving the dry material in distilled water. The solutions were stored at 6–8° C. for at least 10 hours to eliminate air bubbles before use:

Aa: 2.00% (w/w) Sodium Alginate, Sorbalg® PH125 from Danisco Ingredients, Denmark Ab: 2.00% (w/w) Crosslinked carboxymethylcellulose (CMC) AquaSorb® A500 from Aqualon, a Division of Hercules Incorporated Ac: 13.2% (w/w) Calcium chloride dihydrate Ad: 2.00% (w/w) Chitosan, Seacure S244 from Pronova Biopolymer A.S., Norway.

This solution also contained 0.90% (w/w) Acetic acid (glacial 100%) from Merck, Germany.

B: Preparation of a Stock Suspension

Ba: A stock suspension was prepared by suspending 2.00% (w/w) calcium alginate (Calcium alginate PH470 from Danisco Ingredients, Denmark) in distilled. water. The suspension was continuously agitated during storage and use to avoid sedimentation.

C: Preparation of a Sol Gel

A sol gel was prepared by mixing a premix of 40.0 grams of Stock Aa with 40.0 grams of Stock Ab using an Ystral mixer at a speed of 3000 rpm for 2 minutes. The premix was converted into an insoluble Ca/Na alginate gel by adding 140.0 grams of Stock Ba. 3.00 grams of Stock Ac were then added, and mixing was continued for 5 minutes and a homogeneous sol gel was obtained. The sol gel is stable for 48 hours if stored at 6–8° C.

D: Freezing and Dehydration of Sol Gel (Xerogel 1)

The sol gel was frozen into sheets with a thickness of 4 mm comprising a reinforcing net (Net 909 H514 from Smith & Nephew). The morphology was controlled by the method as described in Example 1 of WO 95/05204. To preserve the morphology, the frozen wall structure, the ice sheets were then dehydrated by freeze-drying at 1 hPa for 24 hours.

E: Dry Heat Treatment of Frozen Xerogel (Xerogel 2)

Xerogel 1 was subjected to dry heat treatment at 160° C. for 30 minutes whereby the product is converted into a water swelling but water-insoluble xerogel.

Reference Sample:

Samples having the same chemical composition as Xerogel 2 were produced as described in WO 95/05204. A premix of 1.6% (w/w) of sodium alginate (Sorbalg® PH125, Danisco) and 0.4% (w/w) of crosslinked CMC (Aquasorb® A500, Hercules) in distilled water was frozen into sheets with a thickness of 4 mm comprising a reinforcing net as described above. Then, the ice sheets were freeze dried, ion exchanged using a calcium chloride ethanol solution and dried as described in Example 1 of WO95/05204.

Absorbing Capacity of Physiological Saline:

Four test samples of 4×6 $cm^2$ were prepared, a reference sample of gel before and after ion exchange, Xerogel 1 and Xerogel 2. All samples were immersed in 15 ml of a solution of physiological saline for 30 minutes at ambient temperature in a petri dish. The absorbing capacity was calculated by weighing the sample before and after the immersion. The absorbing capacity was calculated using the formula.

Weight (wet)−Weight (dry)/Weight (dry):

| Absorbing Capacity: | |
|---|---|
| Xerogel 1: | Disintegrates |
| Xerogel 2: | 28–32 g/g dry material |
| Reference (− ion exchange): | Disintegrates |
| Reference (+ ion exchange): | 25–28 g/g dry material |

Gelling Properties:

Both Xerogel 2 and the reference sample subjected to ion exchange showed a sufficient cohesion to be removed from a petri dish in one piece after soaking for 3 hours in physiological saline at 20° C. Xerogel 1 and the reference sample not having been subjected to ion exchange disintegrated.

EXAMPLE 2

This Example shows that the heat treating of the method of this invention renders the net used in Example 1 superfluous as the resulting material shows a sufficient cohesion in itself. Furthermore, the resulting xerogel shows extremely high absorbing capacity.

A Preparation of Xerogels

Three different xerogels were produced by the procedure described in Example 1a–c:

Xerogel a: 100.0 grams of stock Aa+400.0 grams of stock Ab+300.0 grams of stock Ba Xerogel b: 800 grams of stock Ab Xerogel c: 800 grams of stock Ad After mixing the of the sol gels, all samples were frozen without a net and freeze dried by the method mentioned in Example 1. The resulting xerogel samples were then cut into samples of 11×11 cm².

Reference Sample:

A reference sample (Ref a) 11×11 cm² of xerogel a was ion exchanged as mentioned in Example 1. The remaining samples were subjected to a dry heat treatment at 160° C. for 30 minutes, except xerogel c which was dry heat treated at 75° C. for 3 hours.

Absorbing Capacity and Gel Integrity

The absorbing capacity of the samples was measured as described in Example 1.

The following results were found:

| | |
|---|---|
| Xerogel a | disintegrates |
| Xerogel a (ion exchanged) | disintegrates |
| Xerogel a (heat treated) | 28–33 g/g dry material |
| Xerogel b (heat treated) | 40–45 g/g dry material |
| Xerogel c (heat treated) | 35–40 g/g dry material |

EXAMPLE 3

Demonstration of Conservation of the Morphology of the Xerogel by Dry Heat Treatment.

Three samples 11×11 cm2 of Xerogel as prepared in Example 2 were treated by the following methods:

a: no treatment b: subjected to dry heat treatment at 160° C. for 2 hours.

c: subjected to Ion exchange as disclosed under reference in Example 1

Shrinkage and Change of Morphology:

The xerogels subjected to no treatment or subjected to dry heat treatment at 160° C. for 2 hours has retained the same size whereas the xerogel subjected to Ion exchange as disclosed under reference in Example 1 shrunk. As all samples were of the same size before the treatment, it is clear that the heat treatment has no impact on the morphology of the xerogel. At the other hand, the ion exchange treatment re-suited in an excessive shrinkage (as shown on the drawings).

EXAMPLES 4–6

A: Preparation of Stock Solutions

Various stock solutions was prepared by dissolving the dry material stated in distilled water and in one example there were also added some acid. The solutions were stored at 6–8° C.

Da1: 2.00% (w/w) Chitosan, Seacure S244 from Pronova Biopolymer A.S., Norway. This solution also contained 0.90% (w/w) Acetic acid (glacial 100%) from Merck, Germany.

Da2: 2.00% (w/w) Chitosan, Seacure S244 from Pronova Biopolymer A.S., Norway. This solution also contained 1.10% (w/w) Propionic acid (100%) from Merck, Germany.

Da3: 2.00% (w/w) Chitosan chloride, Seacure Cl 210 from Pronova Biopolymer A.S., Norway.

Da4: 2.00% (w/w) Chitosan acetate from Pronova Biopolymer A.S., Norway.

Db: 2.00% (w/w) Sodium Alginate, Sorbalg® PH125 from Danisco Ingredients, Denmark Dc: 2.00% (w/w) GENU pectin type B, rapid set-z from Copenhagen Pectin, a Division of Hercules Incorporated Dd: 2.00% (w/w) GENUVISCO carrageenan type X-0908 from Copenhagen Pectin, a Division of Hercules Incorporated B: Preparation of Sol Gels D1: A sol gel was prepared by mixing a premix of 100.0 grams of Stock Da2 with 150.0 grams of Stock Db with an Ystral mixer at a speed of 3000 rpm for 5 minutes whereafter a homogeneous sol gel was obtained.

D2: A sol gel was prepared by mixing a premix of 100.0 grams of Stock Da1 with 100.0 grams of Stock Dc with an Ystral mixer at a speed of 3000 rpm for 5 minutes whereafter a homogeneous sol gel was obtained.

D3: A sol gel was prepared by mixing a premix of 100.0 grams of Stock Da with 100.0 grams of Stock Dd with an Ystral mixer at a speed of 3000 rpm for 5 minutes whereafter a homogeneous sol gel was obtained.

D4: A sol gel was prepared by mixing a premix of 400.0 grams of Stock Da1 with 60.0 ml distilled water including 2.48 grams of sodium thiosulphate pentahydrate from Merck, Germany with an Ystral mixer at a speed of 3000 rpm for 5 minutes whereafter and a homogeneous sol gel was obtained.

D5: A sol gel was prepared by mixing 100.0 grams of Stock Da1 with 100.0 grams of Stock Db with an Ystral mixer at a speed of 3000 rpm for 5 minutes whereafter a homogeneous sol gel was obtained.

D6: A sol gel was prepared by mixing a premix of 100.0 grams of Stock Da3 and 1.25 grams of sodium acetate with 100.0 grams of Stock Db. The sample was prepared by using a Ystral mixer at a speed of 3000 rpm for 5 minutes whereafter a homogeneous sol gel was obtained.

D7: A sol gel was prepared by mixing 100.0 grams of Stock Da3 with 100.0 grams of Stock Db. The sample was prepared by using a Ystral mixer at a speed of 3000 rpm for 5 minutes whereafter a homogeneous sol gel was obtained.

D8: A sol gel was prepared by mixing a premix of 100.0 grams of Stock Da3 and 0.9 grams of acetic acid with 100.0 grams of Stock Db. The sample was prepared by using a Ystral mixer at a speed of 3000 rpm for 5 minutes whereafter a homogeneous sol gel was obtained.

D9: A sol gel was prepared by mixing 100.0 grams of Stock Da4 with 100.0 grams of Stock Db. The sample was prepared by using a Ystral mixer at a speed of 3000 rpm for 5 minutes whereafter a homogeneous sol gel was obtained.

D: Freezing and Dehydration of Sol Gels/Solutions

The sol gels were frozen into sheets with a thickness of 4 mm. The morphology was controlled by the method as described in Example 1 of WO 95/05204. To preserve the morphology, the frozen wall structure, the ice sheets were then dehydrated by freeze drying at 1 hPa for 24 hours.

E: Dry Heat Treatment of Dehydrated Xerogels

The xerogels were subjected to dry heat treatment at 85° C. for a specific time, whereby the products were converted into water absorbing and optionally swelling, but water insoluble xerogels.

EXAMPLE 4

This example demonstrates what a sample must comprise to obtain a "homogeneous" two component gel.

Test samples of circular plates Ø=43 mm were prepared. The test samples were heated for about 1½ hour at 85° C. All samples were immersed in 15 ml of a solution of physiological saline for 30 minutes at ambient temperature in a petri dish. It was determined whether the gels after absorbing fluid were cohesive and insoluble or whether they disintegrated.

Following results were obtained from the test samples:

| D1–D5 | cohesive and insoluble |
|---|---|
| D6 | cohesive and insoluble |
| D7 | disintegrates |
| D8 | disintegrates |
| D9 | cohesive and insoluble |

EXAMPLE 5

This example demonstrates the absorption and retention capacity of the two component gels.

Three test samples of circular plates Ø=43 mm were prepared. The test samples were heated for about 1 hour at 85° C. All samples were immersed in 15 ml of a solution of physiological saline for 30 minutes at ambient temperature in a petri dish. The absorbing capacity was calculated by weighing the sample before and after the immersion. The absorbing capacity was calculated using the formula.

Weight (wet)–Weight (dry)/Weight (dry):

| Absorbing capacity: | |
|---|---|
| D1: | 61.5 g/g dry material |
| D3: | 46.8 g/g dry material |
| D4: | 26.7 g/g dry material |

Then, the gels were placed on a metal cylinder (diameter 70 mm), on a piece of filter paper (Munktell Analytical filter paper (00H), diameter 110 mm).

A metal cylinder having a diameter of 75 mm and a weight of 2.5 kg was placed upon the gel for one minute. Then the weight of the test sample was measured again ($W_2$).

The retention was then calculated according to the following two formulas:

Retention (g/g dry material)=$(W_2-W_1)/W_1$

Retention (%)=100*Retention (g/g)/Absorption (g/g)

| Retention: | |
|---|---|
| D1: | 43.4 g/g and 70.6% |
| D3: | 17.3 g/g and 38.2% |
| D4: | 7.6 g/g and 31.3% |

EXAMPLE 6

This example demonstrates the gel strength and elasticity of the two component gels.

Three different test samples of 2.5 to 10 cm were prepared. The test samples were heated for about 2 hours at 85° C. After the heat treatment, the samples were wetted across the sample in a width of 5 to 9 mm. Hereafter the samples were one by one positioned in Lloyds LR5K from Loyd instrument limited, UK (push and pull tester). The instrument measured the gel strength and gel elasticity as maximum load and extension at break by pulling one end of the sample at constant speed.

| Gel strength: | |
|---|---|
| D2: | 1.0 N |
| D5: | 1.3 N |
| Gel elasticity | |
| D2: | 21.2 mm |
| D5: | 11.3 mm |

What is claimed is:

1. A method for preparing a wound dressing comprising a non-fibrous porous material which is swellable but not soluble in water, said material consisting essentially of one or more natural or semi-synthetic hydrophilic polymers or one or more hydrophilic polymeric components and one or more pharmaceutical medicaments, which method consists essentially of forming an aqueous solution or a sol gel comprising the hydrophilic polymers or the hydrophilic polymeric components, forming an object of the aqueous solution or the sol gel having a desired shape, dehydrating the aqueous solution or the sol gel leaving a non-fibrous porous material in a solid, porous form, and subjecting the resulting porous material to a dry heat treatment at an elevated temperature of 40 to 220° C. for a period of 1 minute to several hours.

2. The method claimed in claim 1, wherein the hydrophilic polymeric components are dissolved or solubilized in water to provide the sol gel.

3. The method as claimed in claim 2, wherein the aqueous solution or the sol gel is placed on a pre-nucleated freeze plate.

4. The method as claimed in claim 2, wherein the step of dehydrating is conducted by freeze-drying or by solvent extraction.

5. The method as claimed in claim 1, wherein the hydrophilic components are selected from polysaccharides or derivatives thereof, proteins or polypeptides.

6. The method as claimed in claim 5, wherein the hydrophilic components comprise at least two of the following polysaccharides chitin/chitosan or derivatives thereof, calcium/sodium alginate, pectin, pectate, carrageenan, CMC, other derivatives of cellulose, hyaluronic acid, derivatives of starches or chondroitin sulphate or mixtures thereof.

7. The method as claimed in claim 1, wherein at least one of the hydrophilic polymers is a cationic polymer dissolved in an aqueous solution containing an organic mono-, di- or trivalent acid.

8. The method as claimed in claim 1, wherein the hydrophilic component is selected from polysaccharides or derivatives thereof.

9. The method as claimed in claim 8, wherein the hydrophilic component is CMC or a mixture of CMC and an alginate or chitosan or its derivatives.

10. The method of claim 1, wherein the hydrophilic polymers are polyionic/polyfunctional polymers.

11. The method as claimed in claim 10, wherein at least 15% by weight of the polyionic/polyfunctional polymers have the same charge.

12. The method of claim 1, wherein the hydrophilic polymers of hydrophilic polymeric components are pharmaceutical medicaments.

13. The method of claim 1, wherein at least one pharmaceutical medicament is added to the aqueous solution or the sol gel.

14. The method of claim 1, wherein the sol gel is placed on a surface having a surface temperature below freezing point of water or the sol gel.

15. The method of claim 1, wherein the aqueous solution or the sol gel is frozen to provide an ice structure.

16. The method of claim 1, wherein water in the aqueous solution or the sol gel is selectively removed to give the solid materials of the aqueous solution or the sol gel in the form of a porous structure.

* * * * *